US006881416B2

(12) United States Patent
Fry

(10) Patent No.: US 6,881,416 B2
(45) Date of Patent: *Apr. 19, 2005

(54) ALKYL GROUP-SUBSTITUTED ORGANOPOLYSILOXANE GELS

(75) Inventor: Bryan E. Fry, Tecumseh, MI (US)

(73) Assignee: Wacker Chemical Corporation, Adrian, MI (US)

( * ) Notice: Subject to any disclaimer, the term of this patent is extended or adjusted under 35 U.S.C. 154(b) by 237 days.

This patent is subject to a terminal disclaimer.

(21) Appl. No.: 10/118,503

(22) Filed: Apr. 8, 2002

(65) Prior Publication Data

US 2003/0190301 A1 Oct. 9, 2003

(51) Int. Cl.$^7$ .............................. A61K 6/00; A61K 7/00; C08L 83/04; C08K 5/05; C08K 5/54
(52) U.S. Cl. ................. 424/401; 524/862; 524/267; 524/268; 524/379; 524/385; 524/386; 524/588; 524/731; 524/860; 524/861; 524/864; 523/335; 514/844; 514/845; 514/846; 514/847; 514/848; 514/937
(58) Field of Search ..................... 424/401; 524/862, 524/267, 268, 379, 385, 386, 588, 731, 860, 861, 864; 523/335; 514/844, 845, 846, 847, 848, 937

(56) References Cited

U.S. PATENT DOCUMENTS

| 4,980,167 A | 12/1990 | Harashima et al. |
| 4,987,169 A | 1/1991 | Kuwata et al. |
| 5,136,068 A | 8/1992 | Bahr et al. |
| 5,236,986 A | 8/1993 | Sakuta |
| 5,266,321 A | 11/1993 | Shukuzaki et al. |
| 5,412,004 A | 5/1995 | Tachibana et al. |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,854,336 A | 12/1998 | Divone, Sr. et al. |
| 5,859,069 A | 1/1999 | Yanagida |
| 5,936,028 A * | 8/1999 | Medsker et al. ............ 524/506 |

FOREIGN PATENT DOCUMENTS

| EP | 1010715 | 6/2000 |
| EP | 1132430 | 9/2001 |
| WO | WO 97/44010 | 11/1997 |
| WO | WO 98/00102 | 1/1998 |
| WO | WO 98/00103 | 1/1998 |
| WO | WO 98/00104 | 1/1998 |
| WO | WO 98/00105 | 1/1998 |
| WO | WO 98/18438 | 5/1998 |

* cited by examiner

Primary Examiner—Sreeni Padmanabhan
Assistant Examiner—Lauren Q. Wells
(74) Attorney, Agent, or Firm—Brooks Kushman P.C.

(57) ABSTRACT

Organopolysiloxane gel products having a variety of physical forms and which produce a silky feel when applied to the skin are prepared by reacting an unsaturated organopolysiloxane resin, an Si—H functional organosiloxane crosslinker bearing pendant hydrido functionality, a $C_4$ or higher unsaturated hydrocarbon, and optionally, an unsaturated hydrophile component. Products ranging from viscous liquids, creamy gels, pastes, and soft powders may be obtained. The products are highly useful in formulating cosmetic and pharmaceutical products.

30 Claims, No Drawings

ALKYL GROUP-SUBSTITUTED ORGANOPOLYSILOXANE GELS

BACKGROUND OF THE INVENTION

1. Field of the Invention

The present invention pertains to oleaginous alkyl group-substituted silicone gels, processes for their preparation, and use thereof.

2. Background Art

Organopolysiloxanes have been used in numerous cosmetic applications for many years. In some of these applications, for example, organopolysiloxanes such as silicone fluids have been employed, either in their native form as oleaginous carriers for other cosmetic ingredients, or in the form of oil-in-water emulsions. In many of the latter cases, a surfactant is necessary in order to keep the silicone fluid in stable suspension or dispersion. Somewhat more recently, numerous cosmetic formulations have employed creams or pastes which include organopolysiloxane gels containing volatile organosiloxanes.

U.S. Pat. No. 5,654,362 discloses silicone gels prepared by reacting a linear, Si—H functional polysiloxane with an α,ω-diene, for example 1,5-hexadiene, in the presence of a platinum hydrosilylation catalyst and a low molecular weight silicone oil. The reaction is continued until a gel is formed following which the silicone gel may be crumbled into a powder, or by addition of further silicone oil, may form a silicone paste. The products are employed to thicken hydrophobic liquids such as silicone oils to a gel-like consistency. A variety of cosmetic products such as an antiperspirants, deodorants, skin creams, etc., are disclosed. The use of flammable diene hydrocarbons in the preparation is a disadvantage. Moreover, creams formed from solid powders are said not to provide acceptable properties, as indicated by U.S. Pat. No. 4,980,167, wherein such formulations are said to suffer from lack of lubricity. Similar products prepared from α,ω-dienes and polyether-functional siloxanes are disclosed in U.S. Pat. No. 5,136,068. However, preparation of water-in-oil emulsions from these compositions still requires use of a separate emulsifying surfactant.

U.S. Pat. No. 4,987,169 discloses preparation of linear and lightly crosslinked organosiloxanes in the presence of silicone oils to form soft powdery or soft, translucent solid particles. The crosslinked organosiloxanes are preferably prepared employing Si—H and vinyl-functional linear organopolysiloxanes, crosslinked through the aid of a hydrosilylation catalyst. Because of the limited crosslinking of the crosslinked organosiloxanes, the amount of the latter necessary to produce the solid product is high, for example 30 to 50% by weight. The product is thus relatively expensive. The soft powders may be used as thickeners in solubilizing additional silicone oil to form greasy compositions stated to be useful in cosmetics and lubricants. The deficiencies of the '169 patent are attested to in U.S. Pat. No. 5,760,116, which discloses products prepared in two stages, in a first step, preparing a highly crosslinked gel from an Si—H functional organopolysiloxane resin in the presence of a minor amount of low viscosity organopolysiloxane, and in a second step, adding further organopolysiloxane oil into the gel under high shear to produce a clear, highly viscous liquid. The disadvantage of two stage production is clear.

U.S. Pat. No. 5,859,069 discloses a gelatinous external skin treatment composition prepared from an organopolysiloxane elastomer powder having spherical particles with an average particle size of 1.0 to 15.0 μm, a silicone oil, and a polyether-modified silicone. The '069 patent indicates that prior formulations employing silicone resins are unsuitable for such uses, as they leave a filmy feeling on the skin. The polyether-modified, resin-free (linear) silicone is disclosed as being absolutely necessary; and if amounts of less than 1.0% by weight are used, gelation becomes insufficient and the composition becomes unsuitable for use in cosmetics. Gelatinous external skin treatment compositions containing the spherical powder, 5–75% by weight of silicone oil, and 1–20% by weight of polyether-modified silicone are disclosed. Preparation of the elastomer particles is not straightforward, and creams containing solid powders have been viewed as undesirable, as previously discussed.

Polyether-functionalized silicone surfactants are disclosed in U.S. Pat. Nos. 5,412,004 and 5,236,986. In each case, a polyether-functional linear Si—H containing organopolysiloxane is reacted with an α,ω-divinyl organopolysiloxane. A further series of compounds are prepared by cross-linking employing an α,ω-bis(unsaturated) polyoxyalkylene polyether instead of the α,ω-divinylsiloxane. However, gels are not formed, and incorporation of silicone oil into the compositions must be performed using high shear kneading. The products contain a high weight percentage of polyether moieties (ca 15% in the examples). The synthesis must necessarily take place in several steps. The additional step of kneading with silicone oil is disadvantageous. Moreover, the α,ω-bis(unsaturated) polyethers are expensive to prepare.

U.S. Pat. No. 5,811,487 describes low molecular weight siloxane fluids thickened with silicone elastomers prepared by reaction of Si—H functional siloxanes and an α,ω-unsaturated diene hydrocarbon, the Si—H siloxane first having been partially reacted with a monoalkenyl functionalized polyether to provide polyether functionality. The necessity of employing α,ω-dienes is disadvantageous, as previously discussed.

U.S. Pat. No. 5,854,336 discloses a process for preparing cosmetic products which involves feeding a silicone elastomer composition consisting of a silicone rubber and a carrier fluid into a reactor, mixing the composition in the reactor, delivering the composition from the reactor to a high pressure pump, and from there into a device for reducing the particles of rubber into smaller sizes. The device for reducing particle size is preferably a high pressure feed homogenizer, most preferably a sonolator. Use of high pressure pumps and devices such as sonolators increase the expense of the product. Stable emulsions and creams containing water and glycols either cannot be prepared, or are difficult to prepare, due to the incompatibility of the hydrophobic silicone and hydrophilic water/glycols.

EP 0 790 055 A1 discloses compositions containing a partially reticulated elastomeric organopolysiloxane and a fatty component such as a triglyceride for use in skin care or make-up formulas. What is meant by "partially reticulated" is not defined in the specification, which refers to U.S. Pat. No. 5,266,321 for its description of suitable organopolysiloxanes.

Examples of cosmetic formulations employing silicone gels are also disclosed in International PCT Applications WO97/44010; WO98/18438; WO98/00105; WO98/00104; WO98/00103; WO98/00102, and like patents. It can be clearly seen from such patents that the range of formulations includes anti-perspirants, both liquid and solid, facial creams, moisturizers, and other products. It should also be apparent from a review of these references that there are considerable differences between the variety of organosilicone gels. In particular, some of these gels provide an unacceptable oily feeling when such is not desired. Other gels are more difficult to produce, and unnecessarily increase the cost of formulation. It would be desirable to be able to produce gels in a simple fashion from well-recognized readily available, and essentially non-toxic ingredients, to produce a product which avoids the stringiness of other gels, which can be dispersed without the use of extremely high pressure devices such as sonolators and the like, and without extensive high shear kneading, and which may produce cosmetic products devoid of oiliness or filmy sensation when applied to the skin.

Creamy gels prepared by polymerizing vinyl-functional MQ resins, Si—H crosslinker, and unsaturated polyoxyalkylene polyethers is disclosed in U.S. application Ser. No. 09/522,480, filed Mar. 10, 2000. Such gels are ideally suited for forming aqueous creamy gels. Similar compositions with somewhat different compatibility with water and other hydrophilic (hydroxylic) solvents is disclosed in U.S. application Ser. No. 09/317,093, filed May 22, 1999. Both of the foregoing applications are incorporated herein by reference. While the aforementioned creamy gels have a wide variety of uses, they suffer from several drawbacks as well. First, the polyoxyalkylene portion of the molecule, due to its hydrophilic nature, limits the ability to formulate with oleophilic components in some instances. Second, the unsaturated polyoxyalkylene compounds used to prepare the gels tend to be relatively expensive. Third, many of the compositions are strictly limited to gel-like or creamy gel preparations. Finally, the compositions may not provide an ideal feel to the skin when used in cosmetic applications.

It would be desirable to form powders and gel-like products which can be used to broaden the formulation window employed, in particular, by the cosmetics industry.

SUMMARY OF THE INVENTION

It has now been surprisingly discovered that powders and gels may be prepared by reacting an unsaturated organopolysiloxane resin, an Si—H functional crosslinker bearing pendant hydrido functionality, and a modifying moderate to long chain alkene or a cycloalkene, the reaction taking place in the presence of an oleaginous liquid, preferably a volatile silicone or aliphatic or cycloaliphatic hydrocarbon or mixture thereof. That gels, and particularly powders, can be formed rather than only solutions under these circumstances is surprising in view of the presence of the modifying hydrocarbon groups which would be expected to increase solubility in non-polar liquids.

DETAILED DESCRIPTION OF THE PREFERRED EMBODIMENTS

The organopolysiloxane gels of the present invention can be obtained in numerous forms including, but not limited to, moderate to high viscosity liquids, pastes, clear gels, creamy gels, and most surprisingly, high liquid content soft powders. The products may be formulated with numerous ingredients, in particular, ingredients useful in the cosmetics field. These include, for example, water, emollients, humectants such as propylene glycol, dipropylene glycol, glycerine, etc., fatty triglycerides, lanolin, essential oils, natural and synthetic waxes and wax-like components, fragrances, alcohols, oleaginous liquids including natural and synthetic oils, and the like. The products thus have high versatility, and may be useful in many products such as face powders, eye shadow, foundation, lipstick, lip gloss, and the like. These uses are exemplary only, and not limiting. Numerous uses in non-cosmetic areas of technology are possible as well. The powders display high lubricity and a silky feel quite unlike ordinary powder cosmetic ingredients.

The subject invention gels are prepared by the reaction of three components:
A) an unsaturated-functional silicone resin;
B) an Si—H functional organopolysiloxane crosslinker bearing pendant hydrido functionality; and
C) an unsaturated hydrocarbon having four or more carbon atoms, the reaction taking place in an oleaginous component. The reaction is a hydrosilylation reaction which takes place in conjunction with a hydrosilylation catalyst, preferably a platinum-containing catalyst.

The oleaginous component comprises minimally 20 weight percent of the overall composition, preferably minimally 50 weight percent, more preferably 60 weight percent or more, and most preferably in the range of 65 to 90 weight percent. The oleaginous component may be a single component or a mixture of components. The oleaginous component is preferably non-reactive with respect to the other reactive ingredients. However, it is possible to employ oleaginous ingredients which are partially reactive, for example naturally occurring oils or esters or glycerides thereof containing mono- or multiply-unsaturated fatty acids. Preferably, the oleaginous substances are low viscosity and preferably volatile organopolysiloxanes or saturated aliphatic or alicyclic hydrocarbons, or mixtures thereof.

The low viscosity and preferably volatile organopolysiloxane may be a low molecular weight oligomeric polydialkylsiloxane, or a cyclic siloxane, or mixtures thereof. Most preferably, the low viscosity organopolysiloxane is an oligomeric polydimethylsiloxane or a cyclic polydimethylsiloxane. Other alkyl, aryl, alkaryl, and aralkyl groups are also acceptable, of course, for example, phenyl groups, benzyl groups, $C_2-C_{18}$ alkyl groups, and the like. However, because of cost considerations and the ease of formulation, organopolysiloxanes with methyl groups attached to the silicon atoms are highly preferred. Cyclic polydimethylsiloxanes are most preferred. However, linear trimethylsilyl(oxy)-terminated polydimethylsiloxanes having an average from 2 to 50 silicon atoms in the organopolysiloxane backbone may also be used. If volatility is desired, the number of silicon atoms should be greatly restricted, for example, to below 10, and preferably below 6. However, if relatively low viscosity but non-volatile fluids can be tolerated, extensions of the organopolysiloxane backbone to higher numbers of silicon atoms, for example, to 50 or 500 silicon atoms is possible. These non-volatile fluids may have viscosities greater than about 10 cSt, and preferably up to about 2000 cSt. The organopolysiloxanes may also be slightly cross-linked, as long as the cross-linking does not overly increase the viscosity. Viscosity is preferably below 100 cSt, however, more preferably below 10 cSt, and most preferably, in the case of volatile organopolysiloxanes, less than 5 cSt.

Preferably, the organopolysiloxanes are volatile organopolysiloxanes. As indicated previously, volatility can be achieved in linear organopolysiloxanes by selection of oligomeric organopolysiloxanes with at most about 6 to 10 silicon atoms in the organopolysiloxane backbone. Preferably, however, cyclic organopolysiloxanes having from 3 to 6 silicon atoms are utilized, for example, octamethylcyclotetrasiloxane, decamethylcyclopentasiloxane, dodecamethylcyclohexasiloxane, and the like. As with the linear organopolysiloxanes, groups other than methyl groups may be present, for example, $C_2$–$C_{18}$ alkyl groups, preferably $C_{2-4}$ alkyl groups, aryl groups, and the like. In addition, and also as is the case for the linear polysiloxanes, functional groups which do not interfere with the stability of the organopolysiloxane gels or with the ability to use these in cosmetic formulations may be tolerated. In particular, examples include hydroxyl (silanol) groups, alkoxy groups, for example, those which are relatively hydrolytically stable, and the like. Compounds containing reactive groups such as acetoxy groups, methoxy groups, ethoxy groups and the like, should generally be avoided unless they are retained for some special purpose in the cosmetic formulations or used in non-cosmetic applications. It is not desired to include any halo-functional compounds in the organopolysiloxane gels. Please note in this respect that minor amounts of such groups are sometimes unavoidable in organosiloxane resins due to their method of preparation, and these minor amounts are tolerable.

Up to 50 percent by weight of the low molecular weight organopolysiloxane component or even all of this component may be replaced by one or more oleaginous substances. Thus, in the claims, the term "oleaginous composition" is used to describe the oily, hydrophobic component which is added during preparation of the gel. This composition does not include any additional oils which may be later added following preparation of the gel, by dissolution, emulsification, or dispersion following preparation of the gel.

Suitable oily substances include vitamin oils such as vitamins A or E or related compounds such as α-tocopheryl acetate; fatty oils, including ω-3 and ω-6 polyunsaturated fatty acids and their esters, retinol, retinoic acid, esters of the latter retin compounds; vegetable oils such as peanut, olive, palm, cannola, sunflower, and the like; mineral oils; flavoring or "essential" or "aromatic oils" such as the various terpenes both natural and synthetic, patchouli, myrrh, frankincense, lavender, vanillin, sandalwood, eucalyptus, camphor, menthol, and the like, or oily substances such as benzaldehyde, cinnamaldehyde, and the like; and natural and synthetic oils or oil-soluble solids such as various mono-, di- and triglycerides, polyoxyalkylated vegetable oils, lanolin, lecithin, and the like. More preferably, the oleaginous composition contains 70% or more low molecular weight, preferably volatile organopolysiloxanes, more preferably 80% or more, and most preferably 90% or more. Oleophilic solvents, particularly low odor paraffinic solvents which are cosmetically and/or pharmaceutically acceptable and have boiling points below 200° C., preferably in the range of 60° C. to 150° C., may also be part of the oleaginous component, preferably in amounts of less than 50% by weight based on the total weight of this component. These examples are illustrative and not limiting.

The oleaginous substances may also comprise aliphatic and alicyclic hydrocarbons, preferably saturated hydrocarbons. The aliphatic hydrocarbons may be straight chain or branched, and the alicyclic hydrocarbons may constitute unsubstituted cyclic hydrocarbons or aliphatic hydrocarbyl-substituted hydrocarbons. Examples of suitable hydrocarbons include n-heptane, n-octane, isooctane, n-decane, isodecane, n-dodecane, isododecane, cyclohexane, cycloheptane, cyclooctane, methylcyclohexane, dimethylcyclohexane, ethylcyclohexane, nonylcyclohexane, and the like. This list is also illustrative and not limiting.

Suitable oleaginous compounds also include oil-like polyethers such as bis(alkyl) ethers of low molecular weight glycols, and liquid oligomeric and polymeric polyoxyalkylene glycols, their alkyl mono- and di-ethers, and mono- and dialkylesters. It is preferable that the majority of the polyoxyalkylene glycols be prepared from a majority (>50 mol percent) of alkylene oxides having greater than 2 carbon atoms; i.e., propylene oxide, 1,2- and 2,3-butylene oxide, tetrahydrofuran, oxetane, cyclohexene oxide, and the like.

All or a portion of the oleaginous component may comprise one or more essential oils or fragrance oils, such as oil of rosemary, thyme oil, patchouli oil, sandalwood oil, oil of camphor, oil of menthol, etc. Use of perfume oils to form soft powders according to the invention provide a novel vehicle for the formulation of powdery solid, gel-like or creamy gel perfume products.

Numerous admixtures of oleaginous substances may be used, limited only to those compositions which do not phase-separate following preparation of the gel product. It is highly preferred that the oleaginous component be a volatile cyclic or low molecular weight siloxane or organopolysiloxane, or mixtures thereof, a moderate volatility hydrocarbon or hydrocarbon mixture, or a mixture of these siloxanes and hydrocarbons. Particularly useful organosiloxane mixtures are disclosed in U.S. Pat. No. 6,350,440, incorporated herein by reference. These siloxanes have a most useful evaporation profile.

A necessary component of the reaction mixture used to prepare the organopolysiloxane gel is an unsaturated, preferably vinyl functional MQ resin or similar, highly crosslinked resin containing M, Q, and/or T moieties, and optionally a minor amount of D moieties. Such resins are by now well-known in the art. In the organopolysiloxane art, the term "resin" is not applied to polymers in general, but is restricted for the use in describing relatively highly cross-linked and often high molecular weight products produced by the reaction of silanes which are capable of forming three-dimensional networks. The term "M" refers to mono-functional units while the term "Q" refers to tetrafunctional units. In other words, an MQ resin contains predominantly M units wherein silicon is attached to only one oxygen in the cross-linked molecules, and $SiO_{4/2}$ "Q" units wherein each silicon atom is attached to four other oxygen atoms, resulting in a high level of cross-linking. In some MQ resins, small amounts of difunctional $R_2SiO_{2/2}$ and trifunctional $RSiO_{3/2}$ ("D" and "T" units, respectfully), are also present. MQ resins are frequently produced by the hydrolysis of silanes such as tetraethoxysilane, vinyldimethylethoxysilane and trimethylethoxysilane. The resulting MQ resin frequently retains some residual alkoxy functionality as a result of the method of its preparation, and will occasionally include other functionalities such as silanol or halo functionality as well. A preferred MQ resin is MQ resin 804, available from Wacker Silicones Corporation, Adrian, Mich., which contains approximately 1.2 to 1.8 weight percent vinyl functionality. MQ resins having unsaturation other than vinyl, including vinyloxy, allyl, allyloxy, propenyl, etc., are less commonly available, but may be used also. The various unsaturated resins may be used alone or in admixture with other unsaturated resins. Minor amounts of unsaturated non-resinous organopolysiloxanes may be used as well, provided a stable gel can be obtained. The term "resin" is used herein in its customary meaning, i.e. a highly three dimensionally crosslinked polymer containing a majority of M units, and T and/or Q units. MT, MQ, and MQT resins are thus preferred.

The unsaturated silicone resins, as indicated, can contain a variety of hydrosilatable unsaturated groups, including both ethylenic and ethylynic unsaturation. It is preferable, although not mandatory, that the unsaturation be terminal. For example, in hexenyl unsaturated groups, terminal (ω−)

hexenyl groups are preferred. The unsaturated groups may also, as indicated, be unsaturated ether groups such as vinyl ether groups, and may be other heteroatom containing groups as well, i.e. (meth)acryloxy groups. Vinyl and allyl groups are most preferable, as these are commercially more easily obtainable at reasonable cost. However, groups such as ω-hexenyl or ω-octenyl may allow preparation of products with unusual property profiles and uses.

The Si—H functional organopolysiloxane cross-linking agent is a necessary part of the present gel formulation. While Si—H-terminated organopolysiloxanes may be used as crosslinkers, past experience indicates that gels prepared from such compounds may tend to have a stringy appearance or may form only liquid products of low viscosity unless the solids content, i.e., of the non-oleaginous components, is quite high. The modifying alkene used in the present invention, as well as mono-unsaturated polyethers, will react with the terminal Si—H groups thus acting like "chain stoppers," thus, inhibiting the crosslinking reaction. Preferably the crosslinker must comprise, in substantial part, an Si—H functional organopolysiloxane which contains Si—H functional units along its polymer backbone. The Si—H functional organopolysiloxane may or may not, in addition to these Si—H functional units, also include terminal Si—H units. A preferred crosslinker is EL Crosslinker 525, a poly(methylhydrogen)-dimethylsiloxane containing approximately 0.54 weight percent silicon-bonded hydrogen atoms, and having a weight average molecular weight of ca. 29,100 Daltons, measured with a 2-column SEC, refractive index detector, calibrated with polystyrene. The weight average molecular weight of the crosslinker may vary from about 134 Da to preferably 40,000 Da or higher, preferably from 5000 Da to 40,000 Da, and more preferably from 10,000 Da to 35,000 Da. The crosslinkers must contain minimally 3 Si—H bound hydrogens, and preferably contain in excess of 5 Si—H bound hydrogens per molecule, more preferably 10 or more, and most preferably 20 or more.

By the term "pendant hydrido functionality" is meant organopolysiloxanes where at least a portion of the total Si—H functionality is located along the polymer backbone, i.e., in groups such as methylhydrogensiloxy or ethylhydrogensiloxy groups. Terminal Si—H functionality may also be present, so long as pendant hydrido functionality is present as well. It is possible to employ an Si—H functional organopolysiloxanes having only terminal unsaturation, such as dimethylhydrogensiloxy-end capped polydimethylsiloxanes. The useable proportions of such terminal Si—H functional siloxanes is inversely proportional to molecular weight, with larger amounts of α,ω-Si—H functional $Si_2$, $Si_3$, and $Si_4$ di- and oligosiloxanes being useful as compared to higher molecular weight α,ω-Si—H functional organopolysiloxanes.

For reasons of cost, it is preferable that the majority of Si-bound hydrocarbon groups in the Si—H functional crosslinkers be methyl, ethyl, or phenyl groups, preferably methyl or ethyl groups, and most preferably methyl groups. However, other higher molecular weight groups such as isooctyl, nonylphenyl, and the like are also useful. The Si—H functional crosslinkers may also contain alkoxy groups, particularly less reactive higher alkoxy groups such as octyloxy or isooctyloxy groups. While lower alkoxy groups such as methoxy or ethoxy groups are relatively reactive, higher alkyl alkoxy groups are generally far less reactive, many of these being stable in the presence of water for extended periods of time.

The unsaturated hydrocarbon component is a hydrosilylatable hydrocarbon with at least 4 carbon atoms, preferably at least 6 carbon atoms, more preferably at least 8 carbon atoms, and most preferably at least 10 carbon atoms. While there is no fixed upper limit to the number of carbon atoms, it is preferable that the unsaturated hydrocarbon component contain less than 30 carbon atoms, preferably less than 24 carbon atoms. Preferably, the unsaturated hydrocarbon contains between 10 carbon atoms and 24 carbon atoms, more preferably between 12 and 20 carbon atoms.

The unsaturated hydrocarbon component may be straight chain, branched, or cyclic. Examples include, but are not limited to, 1-butene, 1-pentene, 2-butene, 2-pentene, 1-hexene, 2-hexene, 3-hexene, 1-octene, isooctene, 1-decene, 1-dodecene, cyclohexene, methylcyclohexene, hexylcyclohexene, norbornene, camphene, etc. Where the unsaturated hydrocarbon moiety contains greater than 6 carbon atoms, the moiety may contain one or more heteroatoms interspersed along the backbone, i.e., 1-butenyloxybutane, vinyloxyhexane, and the like. In addition, when the hydrocarbon moiety contains in excess of 8 carbon atoms, it may contain a carboxylic acid or ester group, for example linolenic acid or linolenic acid methyl ester, a carboxylic acid amide group, or other polar group. The hydrocarbon moiety must be essentially oleophilic, i.e., preferably has an HLB of less than 4, preferably less than 2 when hydrophilic or polar groups are present. The ratio of carbon atoms in the unsaturated hydrocarbon component to heteroatoms O, N, or S must be at least 4:1, and more preferably 6:1 or more.

Additional hydrosilylatable hydrocarbons may be present also, but are not preferred, and their residues should comprise less than 10 mol percent, preferably less than 5 mol percent based on total unsaturated hydrocarbons of all types present. For example, low molecular weight alkenes such as ethylene, propylene, vinylmethyl ether, vinylethyl ether, and the like may be employed. In cases where an excess of Si—H functionality is employed to achieve higher hydrosilylation conversion of hydrosilylatable groups, excess Si—H functionality may be removed by addition of ethylene or propylene, preferably under pressure. Excess ethylene or propylene may be removed easily from the product due to their low volatility, or left in the product due to their low toxicity.

The subject invention organopolysiloxane gels may also be prepared using an optional unsaturated hydrophile component in addition to the unsaturated hydrocarbon component. Preferably, no such component is employed. However, when employed, the unsaturated hydrophile component and the unsaturated hydrocarbon component may be present in a mol ratio of about 90:10, more preferably, in increasing order, 80:20, 60:40, 40:60, 20:80, 10:90, and 5:95. The unsaturated hydrophile may include a hydrophilic group such as a saccharide or oligo- or polysaccharide, a polyglyceride, a hydrophilic polyoxyalkylene polyether, and the like, or may contain an ionic or other highly polar group.

The hydrophilic function is preferably supplied by a hydrophilic polyether group, or by polar groups such as hydroxyl groups, amide groups, carboxyl groups and their salts, etc. Most preferably, the hydrophilic groups are nonionic hydrophiles such as polyoxyalkylene groups, polyglycol moieties, oligosaccharides, and the like. Polyoxyethylene groups are the preferred hydrophiles, particularly those containing four or more, preferably 4–50, and more preferably 5 to 20 repeating oxyethylene and/or oxypropylene groups, as well as those containing low numbers of oxypropylene groups may also be suitable. Thus, the preferred hydrophiles correspond to the formula $R^1$—O—(R—O)$_n$—$R^2$ where $R^1$ is an unsaturated hydrocarbon, R is an alkylene group, preferably methylene, ethylene, methylethylene, 1,3-propylene or tetramethylene, $R^2$ is H or $CH_3$, and n is from 3 to about 20. Most preferred unsaturated hydrophiles correspond to the formula $$CH_2=CH-CH_2-O-(R-O)_n-R^2$$

where R and $R^2$ are defined as before and n is 4–50, preferably 5–20, and more preferably 5–12, or to methyl capped polyethers of similar structure. The distribution of alkylene groups when different alkylene moieties are present may be random, block, block-random, or any other distribution employed in polyether surfactants. Non-ionic hydrophiles are most preferred.

Preferred hydrophiles are prepared by oxyalkylating allyl alcohol in the presence of basic catalysts to form allyloxy-terminated, ω-hydroxy polyether monols. Allyloxy-functional polyoxyethylene monols are commercially available from Rhodia Inc. as Rhodasurf AAE-10 and from the Dow Chemical Company as AE-400. Both products are nominal five to ten mole oxyethylated allyl alcohol adducts containing a range of oligomers. Also suitable as hydrophiles are oxyethylated unsaturated diols such as oxyethylated 1,4-butenediol and 1,4-butynediol, and oxyethylated unsaturated carboxylic acids, particularly ω-alkenoic acids, or unsaturated diacids such as fumaric acid, maleic acid, and the like. Hydrophiles with carboxylate ester end groups or alkyl ether end groups are also useful, particularly esters of lower $C_{2-4}$ alkanoic acids and ethers of lower $C_{1-4}$ alkanols. Acetates and methoxy and ethoxy ethers are some preferred carboxylate and ether terminal groups. The end groups may also be carboxylic acid groups, sulfonate groups, phosphanate groups, or their esters or salts. The same modifications may be made to other unsaturated hydrophiles.

Also suitable are alkenyl-functionalized polyhydroxy substances such as polyglycerols and oligosaccharides. Polyglycerol, for example, may be functionalized with allyl groups by reaction with allyl chloride to form the polyglycerol allyloxy ether, or with propenoic acid, propenoyl chloride, maleic acid, maleic anhydride, or maleic acid chloride to form the corresponding carboxylic acid ester(s). Syntheses for such compounds may be found in the literature. Functionalization may also be accomplished by reaction with unsaturated isocyanates such as 1-isocyanato-1,1-dimethyl-4-isopropenylbenzene (TMI) or isocyanatoethylmethacrylate. Polyglycerols and oligosaccharides and similar hydrophiles may be modified to contain methoxy, ethoxy, carboxymethyl, or other modifying groups.

The relative amounts of unsaturated silicone resin and unsaturated hydrocarbon may be varied between wide limits depending upon the nature of the product to be obtained. Viscosity of liquid products generally increases with increasing amounts of unsaturated silicone resin and increasing chain length of the unsaturated hydrocarbon employed. Using too low an amount of unsaturated silicone resin will produce low viscosity products of little value, and if gel-like products or solid products are desired, a reasonable amount of unsaturated silicone resin will be required. With a given Si—H functional crosslinker, the amount of unsaturated silicone resin used will in turn limit the amount of other unsaturated ingredients such as unsaturated hydrocarbon which may be used. However, the total amount of hydrosilylatable materials used can be varied somewhat by employing a crosslinker with a higher mol percent (and thus higher weight percent) of Si—H bound hydrogen.

The ratio of moles of unsaturation in the resin to moles of Si—H is preferably in the range of 0.07 to 0.74, more preferably 0.07 to 0.34, and most preferably 0.07 to 0.23. Ratios of 0.13 have proven quite satisfactory when MQ resins are employed. The ratio of moles of hydrocarbon unsaturation to moles of Si—H is preferably in the range of 0.04 to 1.82, more preferably 0.04 to 0.66, and most preferably about 0.29.

A hydrosilylation catalyst is also required. Suitable hydrosilylation catalysts are well-known, and widely available from numerous sources. Preferred hydrosilylation catalysts are platinum compounds such as those disclosed in U.S. Pat. Nos. 3,159,601; 3,159,662; 3,220,972; 3,715,334; 3,775,452; and 3,814,730, and German published application DE 195 36176 A1, preferably supplied in a solvent suitable for use in cosmetic formulations, such as propanediol. Most preferred is Catalyst OL, a divinyl-terminated polydimethylsiloxane platinum complex diluted with polydimethylsiloxane, and available from Wacker Silicones, Adrian, Mich. Other solvents may be used as well for dilution of the catalyst, provided that they are cosmetically acceptable, or can be removed from the gel, for example, by exposure to low pressures or stripping.

Applicants have discovered that the softness of hydrosilylation-type gels may be maintained over time if a minor, but effective amount of a hydrosilylation catalyst inhibitor is added to the formulation, preferably after initial gelation. The catalyst inhibitors may be selected from all hydrosilylation catalyst inhibitors available. However, because the gels are intended for cosmetic formulations, some inhibitors may not be advisable for toxicological reasons, or for customer acceptance. For example, compounds such as dodecanethiol should be avoided due to its odor. However, in perfume-laden cosmetics, or where very small amounts are used, even these inhibitors may be acceptable. The amount of inhibitor generally ranges from about 0.001 to about 2 parts by weight, preferably 0.01 part to 1 part by weight based on a total gel weight of 100 parts. More preferably, 0.05 part to 0.5 part, and most preferably 0.1 part to 0.4 parts are used. The amount is preferably sufficient such that no or only very little noticeable increase in hardness occurs over a two week period of storage at room temperature. While the inhibitors are preferably added following gelation, or following the onset of gelation, the inhibitor may be added at the same time or even before catalyst addition. Additional catalyst may be required in such cases.

The process employed to prepare the products of the present invention may be varied. For example, the unsaturated silicone resin and Si—H functional crosslinker may be first reacted, followed by reaction of the unsaturated hydrocarbon; all ingredients may be simultaneously reacted; or the unsaturated hydrocarbon may be first reacted with the Si—H functional crosslinker followed by reaction with the unsaturated silicone resin. The latter process or a simultaneous reaction process are preferred. Combinations of the above may be used as well.

In the case of the process where the unsaturated hydrocarbon is first reacted with the Si—H functional crosslinker, this reaction may take place neat or in the presence of the oleaginous component. A lower reaction viscosity may aid in completion of the reaction, but higher concentration of unsaturated hydrocarbon per reaction volume may counter this trend. In either case, the reaction of unsaturated silicone resin and Si—H functional crosslinker or partially reacted Si—H functional crosslinker must take place in the presence of the oleaginous component. Otherwise, the desired products will not be obtained.

In a preferred embodiment, a process for the preparation of a powder composition is provided. The process includes reacting an unsaturated organopolysiloxane resin; an Si—H functional organosiloxane crosslinker, at least 25 mol percent of said crosslinker bearing pendant hydrido functionality and containing minimally 5 Si—H groups; an unsaturated hydrocarbon component containing minimally 6 carbon atoms, optionally containing interspersed heteroatoms or heteroatom groups in a ratio of carbon atoms in the backbone of the unsaturated hydrocarbon moiety to heteroatoms of at least 4:1, or a hydrocarbon moiety containing minimally 8 carbon atoms and terminated by a carboxylic acid amide or carboxylic acid ester group. One example of a hetero atom-containing unsaturated hydrocarbon is a diamide or polyamide of an alkylene diamine, a mono- or dicarboxylic acid or mixture thereof, and an unsaturated mono- or dicarboxylic acid. Such products preferably contain no free carboxylic acid groups. Optionally, an unsaturated hydrophile component, the mol ratio of unsaturated hydrophile component to unsaturated hydrocarbon component not exceeding 90:10, may also be present. The reacting of the unsaturated organopolysiloxane resin and the Si—H functional crosslinker takes place in minimally 20 weight percent of liquid oleaginous component, in the presence of a hydrosilylation catalyst, and the ratio of total moles of unsaturated groups present to mol of Si—H bound hydrogen may be from 0.11 to 2.5.

It is especially surprising that powdery gels can be produced at high levels of oleoaginous liquid content. The gel powders may be the immediate product of organopolysiloxane gel synthesis, or may be converted into powder form by milling, for example in a three roll mill. The powders show a surprising silky feel akin to the feeling one might envision from a composition of microscopic ball bearings.

The powder products may be incorporated into formulated products, for example cosmetics, by conventional methods. For example, powder products can be converted to creamy gels by agitation, either under high or low shear. Water, emollients, humectants, colorants, viscosifiers, thixotropes, fillers, etc., may be added. Some of these ingredients can be added prior to formation of the powder, for example, additives which contain few or no hydrosilatable unsaturated groups.

Following milling of the powder to a fine consistency, numerous cosmetic ingredients can be added, such as perfumes, emollients, lanolin, oils, pigments, U.V. absorbers, dyes, etc. Thickeners such as pyrogenic silica and other ingredients may also be added at this point to increase the viscosity of creams to form paste-like products. A hydrophilic liquid may be added prior to or after the addition of these other ingredients to form the emulsions of the subject invention. Water and low molecular weight organic hydrophilic liquids such as glycerine, ethylene glycol, diethylene glycol, triethylene glycol, propylene glycol, and dipropylene glycol may also be used.

The number and type of cosmetic ingredients which may be added is not overly critical, and can be easily selected by one skilled in the art. In the application herein the term "cosmetically acceptable ingredients" includes all ingredients which can be added by a cosmetic formulator which are cosmetically acceptable for use on the skin. Many such ingredients are listed in standard references, for example INTERNATIONAL COSMETIC INGREDIENT DICTIONARY AND HANDBOOK, ©1997, Cosmetic, Toiletry and Fragrance Assoc., Washington, D.C. The formulations may also be used in pharmaceutical formulations, for example in lotions, ointments, etc., or as a matrix or reservoir component in transdermal drug delivery systems.

Suitable fillers include all those commonly employed. All or part of the filler may be added prior to gelation; however, it is highly preferred to form the gel or powder first and to add filler with stirring to obtain a homogenous-appearing mixture. Examples of fillers include fumed or pyrogenic silica, precipitated silica, other silaceous fillers, and in particular silaceous fillers having a BET surface area greater then 50 $m^2/g$; metal silicates, particularly those containing metals of Groups 1 and 2 of the periodic table; diatomaceous earth; precipitated calcium carbonate; fuller's earth; clay minerals, e.g., smectite clays, including bentonite, wollastonite, etc.; kieselguhr; chalk; transparent iron oxides, and the like. Those fillers which are colored can be simultaneously used as pigments herein. Fillers may preferably be employed in amounts of 0.05 to 40 weight percent, more preferably 0.1 to 25 weight percent, and most preferably 0.5 to 10 weight percent. Fillers of high surface area are generally used in lesser amounts than low surface area fillers, due to the viscosity-increasing effect of the former.

The powders and gels produced herein generally and preferably have a % polysiloxane solids of from 15 to 35% burn rate of 0.5 $in_2$/sec (powder), a flash point of 146° F. (63° C.) or higher (gel), a specific gravity just under 1.0, for example between 0.92 and 0.98, a Brookfield viscosity (spindle 6, 2.5 rpm) of 100,000 to 500,000 cPs, in the case of gels. Some gels may be solids, i.e., powdery solids, or may have specific gravities higher than 1.0, i.e., up to about 1.3. When hydrophilic unsaturated hydrocarbons are used, the gels may exhibit water compatibility (stable emulsion) of up to 80% by weight of water based on total emulsion weight, preferably in the range of 20–40%, and a propylene glycol compatibility (stability) of more than 10%, preferably in the range of 20% to 90%. These figures refer to the amount of hydrophilic liquid, on a weight/weight basis, which can be added and yet form a stable hydrophilic liquid-containing emulsion.

The powders and gels of the subject invention may be used in all cosmetic formulations where silicone emulsions and other products have been used in the past, including, without limitation, skin care products such as antiperspirants, deodorants, sun care, after sun care, moisturizers, creams and lotions; color cosmetic products, such as facial powder, eye powder, eye shadow, liquid foundation, liquid-to-powder foundations, and lipsticks; and hair care products such as hair conditioners, volume enhancers, and the like.

Having generally described this invention, a further understanding can be obtained by reference to certain specific examples which are provided herein for purposes of illustration only and are not intended to be limiting unless otherwise specified.

Gel Preparation, General Procedures A,B,C

A 1000 ml glass reaction kettle is fitted with dessicator-capped condenser, heating mantle, metal stirrer, and temperature controller. The silicone and oleaginous components (volatile or low viscosity fluid, inert diluent, etc.), unsaturated hydrocarbon-functional silicone resin, and silicone crosslinker are added and stirred until homogenous. The unsaturated hydrocarbon is then added and stirred, followed by the hydrosilylation catalyst. The kettle is heated to 75° C. with stirring and maintained at that temperature until gel formation occurs. It is then stirred for one hour more, following which the product mixture is cooled to 40° C., and inhibitor or catalyst poison, if used, is added. The gel is then homogenized using a high shear mixer (Turrax® mixer). This is Procedure A.

Procedure B is similar to Procedure A, but the oleaginous component, crosslinker, and unsaturated hydrocarbon are added and stirred, the catalyst is added, and the reaction mixture temperature raised, while stirring, to 75° C. The unsaturated resin is then added quickly. The remainder of Procedure B mirrors Procedure A.

Procedure C is similar to Procedure B, but only half the catalyst is added initially, the remainder being added at the same time as the resin.

EXAMPLES 1–8

A series of gels were produced employing Procedures A, B, and C. The materials used, their amounts, and the properties of the gels produced are reproduced in Tables 1 and 2 below. Example C7 is a Comparative Example employing no unsaturated alkene.

was added and the reactor heated to 225° C. for 2 hours. The trap was again emptied, and the reactor heated to 225° C. under vacuum for 2 hours to remove excess acid. The product is the undecyclenic acid/octanoic acid diamide of hexamethylenediamine.

To a glass 500 mL kettle was added 300 g octamethylcyclotetrasiloxame, 31.1 g Si—H functional organopolysiloxane Crosslinker 525 (Wacker Chemicals) and 40.0 g of the unsaturated polyamide prepared above. The mixture was stirred and heated to 110° C. and maintained until the solid amide was melted and dissolved. 0.20 g catalyst, Catalyst OL (Wacker Chemicals) was dissolved in 5 g octamethylcyclotetrasiloxane. Half the total catalyst was added while stirring at 300 rpm, and held for 30 minutes. The remainder of the catalyst was then added and 28.7 g

TABLE 1

ALKYL ELASTOMER GEL FORMULATIONS

| Example: | 1 | 2 | 3 | 4 | 5 | 6 |
|---|---|---|---|---|---|---|
| Oleaginous Component[1] | 74.9 | 74.9 | 69.9 | 69.9 | 69.9 | 67 |
| Unsaturated Organopolysiloxane Resin (% wt)[2] | 16.96 | 15.96 | 15.56 | 15.76 | 15.96 | 13.73 |
| Si-H Functional Crosslinker[3] | 2.99 | 3.99 | 4.39 | 4.19 | 3.99 | 13.73 |
| 1-octadecene | 5 | 5 | 10 | 10 | 10 | 5.5 |
| Catalyst OL[4] | 0.0500 | 0.0500 | 0.0500 | 0.0500 | 0.0500 | 0.0500 |
| F950A[5] | 0.10 | 0.10 | 0.10 | 0.10 | 0.10 | 0 |
| Batch Size (g) | 450 | 3700 | 450 | 450 | 450 | 450 |
| Initial % H | 0.0152 | 0.0203 | 0.0224 | 0.0214 | 0.0203 | 0.07 |
| Mol Alkyl Vi/mol H | 1.30 | 0.91 | 1.65 | 1.73 | 1.82 | 0.29 |
| Mol Resin Vi/mol H | 0.74 | 0.53 | 0.47 | 0.49 | 0.53 | 0.13 |
| Viscosity (cP) | 92000 | 504000 | 284000 | 190,000,000 | 101000 | — |
| Characteristics | slimy gel | pasty | creamy | thick slime | stringy | soft[6] powder |
| % H (final) | 0.0038 | 0.0050 | 0.011 | 0.0018 | 0.0028 | 0.037 |
| Procedure Used (A, B, or C) | A | A | A | A | A | C |

[1]CM040, volatile cyclic dimethylsiloxane available from Wacker Silicones, Adrian, MI; [2]MQ resin 804, Wacker Silicones; [3]EL Crosslinker 525, Wacker Silicones; [4]Platinum hydrosilylation catalyst, Wacker Silicones; [5]mercaptopropyl silsesquioxane; [6]2x through a 3-roll mill.

TABLE 2

ALKYL ELASTOMER GEL FORMULATIONS

| Example: | C7 | 7 | 8 | 9 | 10 | 11 | 12 |
|---|---|---|---|---|---|---|---|
| Oleaginous Component[1] | 78.7 | 70.0 | 73.0 | 70.4 | 67.0 | 67.0 | 67.0 |
| Unsaturated Organopolysiloxane Resin (% wt)[2] | 15.3 | 9.77 | 12.57 | 14.02 | 10.22 | 10.22 | 13.74 |
| Si-H Functional Crosslinker[3] | 5.9 | 13.49 | 8.38 | 9.83 | 15.73 | 15.73 | 5.50 |
| 1-octadecene | 0 | 6.7 | 6 | 5.7 | 7 | 7 | 13.74 |
| Catalyst OL[4] | 0.0544 | 0.0500 | 0.0500 | 0.0500 | 0.0500 | 0.0500 | 0.0300 |
| F950A[5] | — | 0 | 0 | — | — | — | — |
| Batch Size (g) | 423 | 450 | 450 | 450 | 450 | 450 | 3700 |
| Initial % H | 0.0301 | 0.0688 | 0.0427 | 0.0501 | 0.0802 | 0.0802 | 0.0700 |
| Mol Alkyl Vi/mol H | 0 | 0.36 | 0.52 | 0.42 | 0.32 | 0.32 | 0.29 |
| Mol Resin Vi/mol H | 0.34 | 0.10 | 0.20 | 0.19 | 0.09 | 0.09 | 0.13 |
| Viscosity (cP) | — | low | 650 | — | — | — | — |
| Characteristics | chunky, separated | powder[6] | powder[6] | soft powder[6] | soft powder[6] | soft powder[6] | soft powder[6] |
| % H (final) | — | 0.035 | 0.009 | 0.028 | 0.047 | 0.051 | 0.046 |
| Procedure Used (A, B, or C) | A | C | C | B | B | C | B |

[1]CM040, volatile cyclic dimethylsiloxane available from Wacker Silicones, Adrian, MI; [2]MQ resin 804, Wacker Silicones; [3]EL Crosslinker 525, Wacker Silicones; [4]Platinum hydrosilylation catalyst, Wacker Silicones; [5]mercaptopropyl silsesquioxane; [6]2x through a 3-roll mill.

EXAMPLE 13

An unsaturated amide was prepared by mixing 80 g hexamethylenediamine, 43 g water, and 50 g octanoic acid, heating to 225° C., and holding for 2 hours in a glass reactor fitted with a trap. The reactor was allowed to cool, and the trap emptied. The reactor was heated to 220° C. under vacuum to remove unreacted hexamethylenediamine, cooled, and the trap again emptied. 93 g undecyclenic acid was added and the reactor heated to 225° C. for 2 hours. The unsaturated organopolysiloxane resin, MQ resin 804, was added with stirring and held for an additional hour. 0.40 g F950A inhibitor was added following gellation. The mol ratio of resin unsaturation to mol Si—H in the crosslinker was 0.12, while the mol ratio of unsaturated polyamide to mol Si—H was 0.67. An opaque paste was obtained upon cooling to 80° C., which softens upon contact with the skin.

EXAMPLE 14

A creamy cosmetic foundation was prepared by blending at 50° C. and 350 rpm, 28.75 g of the powder of Example 12, 28.75 g Wacker-Besil RG 100, a dimethicone/vinyltrimethylsiloxysilicate crosspolymer, 7.5 g Wacker-Besil DM5 dimethicone, and 50 g Wacker-Besil SPG 128, a capryldimethicone ethoxy glucoside/cyclopentasiloxane. To this blend, 10 g Hostaserin DGI, and 15 g NF white beeswax was added at 70° C. while stirring. A pigment blend consisting of 10.25 g white C9729, 2.35 g yellow SAT-Y-77492, 0.45 g blue SAT-UB-7707, 0.95 g red SAT-R-77491 and 85 g Ultra Talc 4000 were added and stirred for 10 minutes at 70° C. An Ultra-Turrax® mixer was then used to thoroughly disperse the pigments. A solution of 10 g sodium chloride in 250 g water was added slowly with conventional stirring, and the blend processed twice through a three roll mill. A smooth cream is obtained.

EXAMPLES 15 AND 16

A sun screen cream and sun screen lotion were prepared by separately mixing the Part A and Part B ingredients identified below, heating each component to 80° C., mixing the A and B components together and cooling to 45° C. The C components were then added while stirring, the mixture cooled, and processed once on a three roll mil.

TABLE 3

| Ingredient | Example 15 | Example 16 |
|---|---|---|
| PART A | | |
| Eusolex 4360[1] | 3 g | 5 g |
| Cetyl alcohol | 4 g | 2 g |
| Parsol MCX[2] | 3 g | 10 g |
| Stearic acid | 8 g | 12 g |
| Wacker-Besil DM350[3] | — | 7 g |
| Dermal IPM[4] | — | 2 g |
| Luviskol VA64[5] | — | 4 g |
| PART B | | |
| Glycerol | 4 g | — |
| Triethanolamine | 1.8 g | — |
| Natrasol 250 HHRCS[6] | — | 1 g |
| Water | 156.2 g | 124 g |
| PART C | | |
| Powder of Example 12 | 20 g | 32 g |
| triethanolamine | — | 5 g |
| Product Characteristic | smooth white cream | white lotion |

[1]benzophenone-3; [2]ethylhexylmethoxycinnamate; [3]dimethicone; [4]isopropyl myristate; [5]PVP/VA copolymer powder; [6]hydroxyethyl cellulose While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention. The terms "a" or "an" mean "one or more" unless the context requires otherwise. Ordinarily, use of the singular or plural of a given type of component implies the respective plural or singular.

What is claimed is:

1. A process for the preparation of a gel composition, said process comprising reacting:
   a) an unsaturated organopolysiloxane resin;
   b) an Si—H functional organopolysiloxane crosslinker, containing minimally 5 Si—H groups;
   c) an unsaturated hydrocarbon component containing minimally 6 carbon atoms, and optionally containing interspersed heteroatoms or heteroatom groups in a ratio of carbon atoms in the backbone of the unsaturated hydrocarbon moiety to heteroatoms of at least 4:1, or said hydrocarbon moiety containing minimally 8 carbon atoms and terminated by a carboxylic acid amide or carboxylic acid ester group; and
   d) optionally, an unsaturated hydrophile component, the mol ratio of unsaturated hydrophile component to unsaturated hydrocarbon component not exceeding 90:10, in the presence of a hydrosilylation catalyst;
   wherein reacting of said unsaturated organopolysiloxane resin and said Si—H functional crosslinker takes place in minimally 20 weight percent of liquid oleaginous component, and wherein the ratio of total mol of unsaturated groups present to mol of Si—H bound hydrogen is from 0.11 to 2.5.

2. The process of claim 1, wherein unsaturated hydrophile is present.

3. The process of claim 1, wherein said unsaturated organopolysiloxane resin is an MQ, MT, or MTQ resin, optionally containing less than 10 mol percent D units with respect to the mol percent of M units present.

4. The process of claim 1, wherein said organopolysiloxane resin is a vinyl-functional resin.

5. The process of claim 1, wherein said Si—H functional crosslinker is a (methylhydrogen)(dimethyl)polysiloxane containing on average 10 or more of Si—H groups per molecule.

6. The process of claim 1, wherein said unsaturated hydrocarbon is a $C_{10}$–$C_{24}$ unsaturated linear or branched alkene.

7. The process of claim 1, wherein said oleaginous component comprises a volatile cyclic siloxane, a low viscosity and optionally volatile linear organosiloxane, a volatile aliphatic or alicyclic hydrocarbon, or mixture of any of these oleaginous components.

8. The process of claim 1, wherein said gel composition is a powder.

9. The process of claim 1, wherein said gel composition is a creamy gel or a paste.

10. An organosiloxane gel composition containing minimally 20 weight percent of a liquid oleaginous component, said gel composition prepared by the process of claim 1.

11. An organosiloxane gel composition containing minimally 20 weight percent of a liquid oleaginous component, said gel composition prepared by the process of claim 2.

12. An organosiloxane gel composition containing minimally 20 weight percent of a liquid oleaginous component, said gel composition prepared by the process of claim 3.

13. An organosiloxane gel composition containing minimally 20 weight percent of a liquid oleaginous component, said gel composition prepared by the process of claim 4.

14. An organosiloxane gel composition containing minimally 20 weight percent of a liquid oleaginous component, said gel composition prepared by the process of claim 5.

15. An organosiloxane gel composition containing minimally 20 weight percent of a liquid oleaginous component, said gel composition prepared by the process of claim 6.

16. An organosiloxane gel composition containing minimally 20 weight percent of a liquid oleaginous component, said gel composition prepared by the process of claim 8.

17. In a cosmetic or pharmaceutical composition wherein an organopolysiloxane gel component is employed in formulating said cosmetic or pharmaceutical composition, the improvement comprising selecting as said organopolysiloxane gel the gel composition of claim 10.

18. The composition of claim 17, wherein a fragrance oil is employed as at least a portion of said oleaginous component.

19. The composition of claim 17, wherein water or a low molecular weight hydrophilic organic compound is emulsified into said gel composition.

20. The composition of claim 17, wherein said gel composition is in the form of a powder.

21. The process of claim 1, wherein said crosslinker b) comprises an organopolysioxane wherein at least 25 mol percent of siloxy units along the polymer backbone of said organopolysiloxane bear Si-bound hydrogen.

22. The process of claim 2, wherein said crosslinker b) comprises an organopolysiloxane wherein at least 25 mol percent of siloxy units along the polymer backbone of said organopolysiloxane bear Si-bound hydrogen.

23. The process of claim 3, wherein said crosslinker b) comprises an organopolysiloxane wherein at least 25 mol percent of siloxy units along the polymer backbone of said organopolysioxane bear Si-bound hydrogen.

24. The process of claim 5, wherein said crosslinker b) comprises an organopolysiloxane wherein at least 25 mol percent of siloxy units along the polymer backbone of said organopolysiloxane bear Si-bound hydrogen.

25. The process of claim 6, wherein said crosslinker b) comprises an organopolysiloxane wherein at least 25 mol percent of siloxy units along the polymer backbone of said organopolysiloxane bear Si-bound hydrogen.

26. An organopolysiloxane gel composition prepared by the process of claim 21.

27. An organopolysiloxane gel composition prepared by the process of claim 22.

28. An organopolysiloxane gel composition prepared by the process of claim 23.

29. An organopolysiloxane gel composition prepared by the process of claim 24.

30. An organopolysiloxane gel composition prepared by the process of claim 25.

* * * * *

UNITED STATES PATENT AND TRADEMARK OFFICE
CERTIFICATE OF CORRECTION

PATENT NO. : 6,881,416 B2
DATED : April 19, 2005
INVENTOR(S) : Bryan E. Fry

It is certified that error appears in the above-identified patent and that said Letters Patent is hereby corrected as shown below:

Column 16,
Line 10, delete "in the presence of a hydrosilylation catalyst" and insert -- in the presence of a hydrosilylation catalyst --.

Signed and Sealed this

Twenty-seventh Day of September, 2005

JON W. DUDAS
*Director of the United States Patent and Trademark Office*